United States Patent
Nemirow

(10) Patent No.: US 6,796,685 B1
(45) Date of Patent: Sep. 28, 2004

(54) VARIABLE COLOR LIGHTING WITH LINEAR FLUORESCENT LAMPS

(75) Inventor: Arthur T. Nemirow, Carson City, NV (US)

(73) Assignee: Bruce Industries, Inc., Dayton, NV (US)

( * ) Notice: Subject to any disclaimer, the term of this patent is extended or adjusted under 35 U.S.C. 154(b) by 0 days.

(21) Appl. No.: 10/075,836

(22) Filed: Feb. 13, 2002

(51) Int. Cl.[7] .................................................. F21V 9/00
(52) U.S. Cl. ........................ 362/293; 362/284; 362/324
(58) Field of Search ................................ 362/224, 293, 362/283, 284, 324, 271, 260, 222, 223, 242, 257, 2, 510; 359/891

(56) References Cited

U.S. PATENT DOCUMENTS

| | | | | |
|---|---|---|---|---|
| 3,805,053 A | * | 4/1974 | Julinot | 362/223 |
| 4,186,431 A | * | 1/1980 | Engel et al. | 362/223 |
| 4,991,070 A | * | 2/1991 | Stob | 362/223 |
| 4,996,632 A | * | 2/1991 | Aikens | 362/560 |
| 5,311,687 A | * | 5/1994 | Reed | 40/502 |
| 5,329,435 A | * | 7/1994 | McGuire | 362/293 |
| 6,210,023 B1 | * | 4/2001 | Evans | 362/284 |

* cited by examiner

*Primary Examiner*—Stephen Husar
*Assistant Examiner*—Bao Q. Truong
(74) *Attorney, Agent, or Firm*—Brooks Kushman P.C.

(57) ABSTRACT

A variable color filter for fluorescent lamps has a color tube supporting colored filter strips disposed longitudinally along the color tube so that the strips are circumferentially adjacent to each other. A motor rotates the color tube inside a mask so that an aperture in the mask limits emission to light filtered by only a circumferential portion of the color tube. A controller positions the color tube in relation to the aperture to achieve a desired coloring of light emitted by the lamp tube.

28 Claims, 5 Drawing Sheets

VARIABLE COLOR LIGHTING WITH LINEAR FLUORESCENT LAMPS

BACKGROUND OF THE INVENTION

1. Field of the Invention

This invention generally pertains to the field of interior lighting and more particularly relates to an electromechanical color control system for linear fluorescent lamps, particularly for use in accent or mood lighting.

2. State of the Prior Art

It is known that people respond at a subconscious level to changes in color and intensity of ambient illumination. For example, slowly dimming light which also changes from white light through increasingly deep shades of blue to darkness is perceived as an end-of-day or nightfall time, bringing about a change in mood conducive to relaxation and eventual sleep. Conversely, a slow increase in illumination from darkness shifting through deep yellow through increasingly brighter shades of yellow to full white light brings about a gradual, natural arousal of a sleeping or resting individual to a state of wakefulness in a manner analogous to waking in response to daybreak and sunrise. These subliminal responses are deeply ingrained in the human and indeed the animal physiology as a result of long evolution, and such changes in illumination are more gentle and harmonious than abrupt turning on or off of interior lights. These benefits have been recognized and exploited in lighting systems of various types, ranging from movie theater lighting to waking clocks equipped with room light controls. These benefits have also been recognized by the airline industry, and efforts have been made to equip passenger aircraft with centrally controlled accent lighting systems for providing a more natural transition in cabin Illumination between daytime and nighttime conditions, and thereby facilitate the passengers transition from wakefulness to sleep and back to wakefulness during long flights.

Effective mood lighting calls for control over both light color and intensity. Color control of artificial lighting under electronic control has been developed particularly by theater/stage lighting equipment manufacturers largely using incandescent light sources. Strips or sheets of colored film are scrolled in front of the light source, and the film transmits only the color of interest. Motorized spools are used to pull scrolls made up of successive sheets of different colored film to achieve a desired sequence of colors. Particular colors can be selected by electronic control of the spools.

Fluorescent lamps have a different shape or form factor than incandescent lamps, in that the former have linear shapes while the latter are doser to point sources of light. The linear fluorescent lamps or tubes produce light by means of an arc discharge in a partially evacuated glass tube. The arc discharge results in emission of certain wavelengths which in themselves are not desirable for general illumination. The interior of the glass tube is coated with a fluorescent compound which emits white light when subjected to the arc discharge emissions. Fluorescent lamp tubes have an elongated shape in order to achieve a sufficient light emitting area along the tube, because the intensity of light emitted by a short tube is usually inadequate for interior lighting. Recently, so called compact fluorescent lights have become available, consisting of long, small diameter fluorescent lamp tubes bent to a compact shape. However, many applications remain for straight fluorescent lamp tubes of various lengths and diameters.

Airliners make extensive use of linear fluorescent lamps for cabin illumination and no simple, effective and economical system for controlling color of linear light sources is available. Scrolling rolls of colored film between two spools in front of a fluorescent tube is not a practical solution for mood or accent lighting applications. In one alternate approach, multiple lamp tubes of different colors are provided, and the net color output is controlled by adjusting the relative light intensity of the various tubes. This approach requires three lamp tubes with separate ballasts for controlling power to each of the tubes and is therefore costly, complex and weighs more than a single tube solution. It is also difficult to diffuse and blend the different colors into a homogeneous white light. In an effort to alleviate these shortcomings, another approach uses white fluorescent lamps in combination with colored light emitting diodes (LEDs). As the white lamp tube is dimmed the appropriate combination of colored LEDs is powered up to provide the desired effect. This approach is deficient in that the LEDs are expensive and not very bright yet consume considerable power, separate power supplies are required for the lamp tube and the LEDs, the different colored light sources are hard to diffuse into even illumination, and the quality of white light is compromised.

A continuing need exists for simpler color control of linear fluorescent lamps.

SUMMARY OF THE INVENTION

This invention addresses the aforementioned need which provides a variable color linear fluorescent lamp suitable for accent or mood lighting of aircraft cabin interiors and other interior lighting applications. The variable color lamp has a lamp base on which is mounted a lamp tube between opposite end sockets, and a color tube supporting a number of colored filter strips each disposed longitudinally along the color tube and in circumferentially adjacent relationship to each other. The color tube is supported for rotation about the lamp tube, and a motor is provided for rotating the color tube. A mask defines an aperture for limiting light emission by the lamp fixture only to light filtered by a selected circumferential portion of the color tube. A color control system is operatively connected to the motor for selectively positioning the color tube in relation to the aperture thereby to select the desired coloring of light emitted from the lamp housing.

The mask may be interposed between the color tube and the lamp tube. Alternatively, the mask may be positioned exteriorly to the color tube. The filter strips are preferably of even width with each other, and may be each of a single color, which color may vary in color density across a strip width.

In one form of the invention adapted for simulation of nightfall and daybreak illumination at least one of the filter strips is substantially opaque to transmission of light and at least one other of the strips is substantially clear. One or more colored filter strips are circumferentially interposed between the opaque and the clear strips. The colored strips may comprise a yellow filter strip and a blue filter strip, preferably of graduated density and increasing in density from the clear filter strip towards the substantially opaque strip.

The filter strips may be affixed to the tube with an adhesive, by a shrunk wrapper or by printing onto a surface of the tube. The filter strips may be, for example, gel filter strips or dichroic filter strips. In some cases it may be desirable to provide an ultra violet filter interposed between the filter strips and the lamp tube.

The color control system is operative for rotating the color tube from the initially selected dear filter to the opaque filter passing through at least one colored filter strip and then again to the dear filter passing through a second colored filter strip at a relatively slow rate not readily perceptible to a human observer thereby to achieve slow changes in intensity and color of illumination suggestive of nightfall and daybreak.

In one particular application, this invention discloses a method for simulating daybreak and nightfall ambient illumination comprising the steps of providing a linear fluorescent lamp including a lamp tube, providing a lamp aperture for emitting light from the lamp tube into an illuminated environment, and filtering light emitted through the aperture through filter media of gradually changing density of color suggestive of nightfall and daybreak respectively between blocked and unfiltered conditions of the emitted light The step of filtering light comprises selectively rotating a number of light filters including a substantially clear filter, a substantially opaque filter, a yellow filter and a blue filter, into alignment or registry with an aperture arranged for limiting emission of light to light filtered through a selected portion of the filter media, comprising one or more of the light filters. In a presently preferred embodiment the yellow filter and the blue filter are each interposed between the clear filter and the opaque filter over the circumference of a cylindrical color tube rotatable about a concentrically supported lamp tube, and wherein the yellow filter and the blue filter are each of increasing density from the clear filter towards the substantially opaque filter.

In an alternate form of the invention, mechanical dimming of a linear fluorescent tube is achieved by dispencing with the color filter strips of the color tube and providing a dimming tube which is clear with only an opaque longitudinal strip of sufficient circumferential dimension to substantially block emission of light when the opaque strip is brought into registry with the mask aperture. Initial positioning of the dimming tube so as to align only the clear portion with the mask aperture allows substantially unimpeded passage of light emitted by the lamp tube and full intensity illumination by the light fixture. Rotation of the dimming tube gradually and increasingly brings the opaque strip into partial registry with the mask aperture, thereby blocking light emission to an increasing extent. When the opaque strip is brought into full registry with the mask aperture light emission is substantially fully blocked and the lamp fixture is in a dark state although the lamp tube is turned on. Between the full illumination and dark states of the lamp fixture close, precise control of light intensity is readily achieved by rotational positioning of the dimming tube.

These and other improvements, features and advantages will be better understood by reference to the following detailed description of the preferred embodiment and the accompanying drawings.

DETAILED DESCRIPTION OF THE PREFERRED EMBODIMENTS

Figure 1:
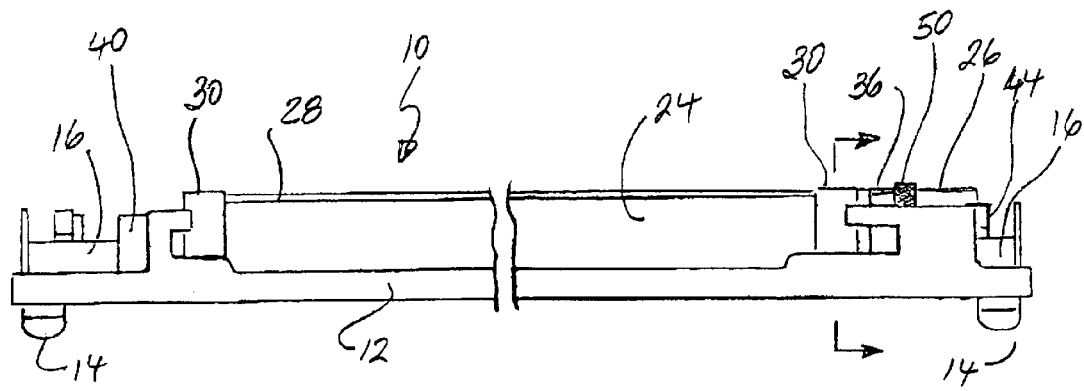
FIG. 1 is a side elevational view of a linear fluorescent light fixture equipped with the color control system of this invention.

With reference to the drawings wherein like elements are designated by like numerals, FIG. 1 shows a linear fluorescent lamp light fixture of a type which is installed along the interior of a passenger airliner cabin for illumination of the cabin interior. The light fixture, generally designated by numeral 10 has a base 12 which is fastened to a mounting surface such as a side wall of an airliner passenger cabin by means of mounting dips 14. A pair of end sockets 16 support between them a linear fluorescent lamp tube 20. A lamp ballast 18 converts a.c. line power to voltages suitable for powering the lamp tube 20 (shown in FIGS. 3–6). Appropriate wiring and cabling (not shown) is provided for supplying line power to light fixture 10 and for connecting the ballast 18 to end sockets 16.

The light fixture 10 is equipped with a variable color filter and control system according to this invention, as will be explained with reference to FIGS. 2 through 6. The variable color filter includes a color filter tube 22, an aperture mask 24 and a motor drive 26 for turning the color filter tube 22 relative to the aperture mask 24. In the embodiment of FIGS. 2–6 the aperture mask 24 is an aperture tube best seen in FIG. 7, in which is defined a longitudinal slot aperture 28. The slot aperture 28 may be defined by application of a black or opaque covering 25 to the inner or outer surface of color filter tube 22 of clear material such as clear polycarbonate plastic, leaving an uncovered clear strip area as slot aperture 28.

Figure 2:
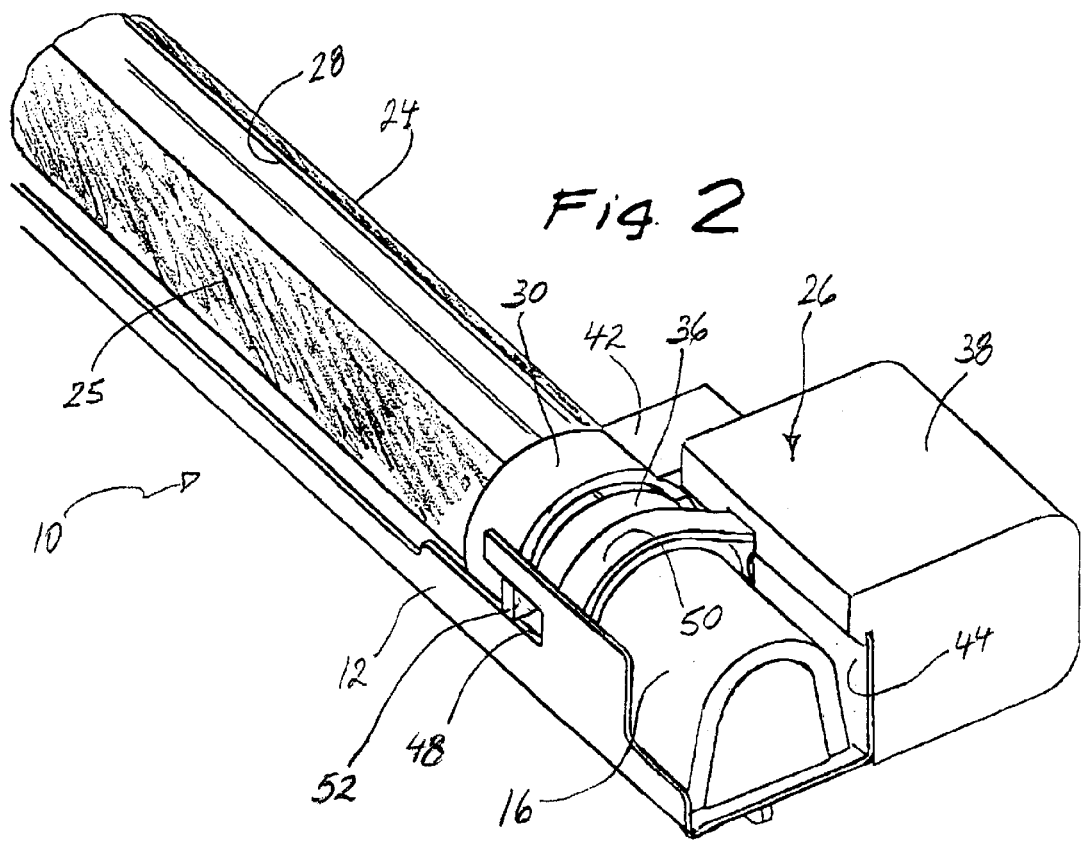
FIG. 2 is a fragmentary perspective view of the light fixture of FIG. 1 showing the motor drive coupled to one end of the color filter tube.
Figure 6:
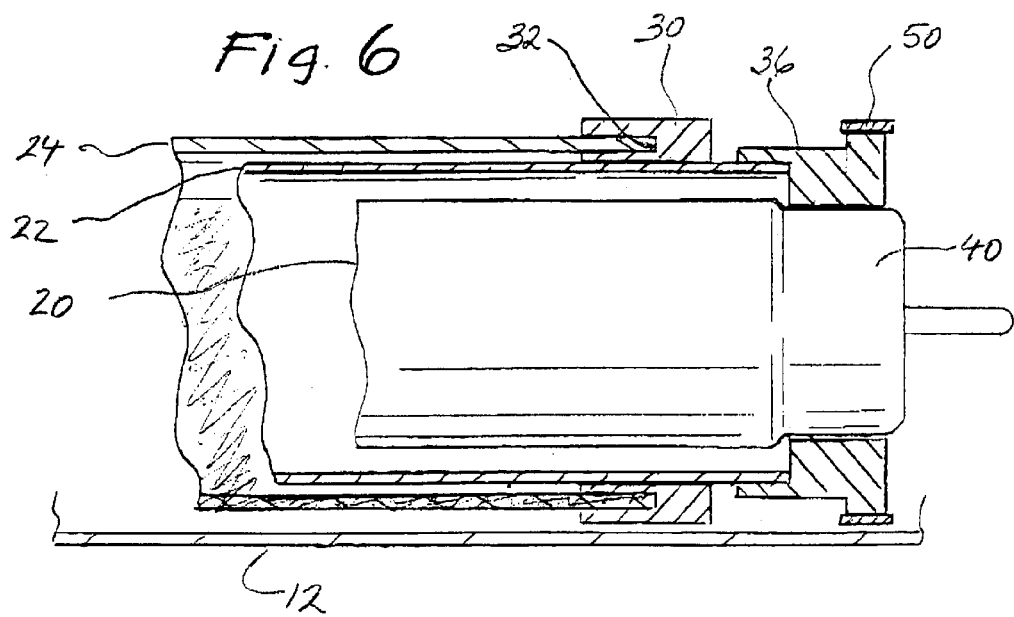
FIG. 6 is a longitudinal section of the color tube and aperture tube supported around the linear fluorescent lamp tube.
Figure 7:
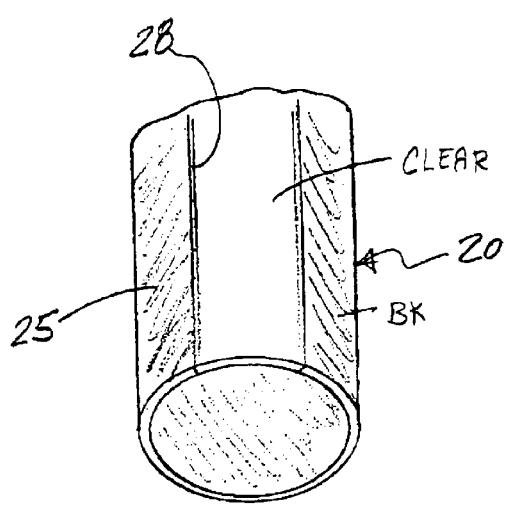
FIG. 7 is a fragmentary side-end perspective view of the aperture tube of the light fixture of FIGS. 2 through 6.

The aperture tube is somewhat shorter than the length of lamp tube 20 and is supported at its opposite ends between a pair of collars 30. The two collars are mounted on the lamp base 12 and define mutually facing annular slots 32, shown in FIGS. 4 and 6. The lamp tube 20 passes through collar openings 34 in the collars 30 to reach end sockets 16. The color filter tube 22 makes a sliding fit inside collar openings 34 and is supported in the collars 30 for rotation about the lamp tube 20. The driven end of the color filter tube 22 is fitted with a drive ring 36 which turns on the existing metallic end cap 40 of the lamp tube 20. The drive ring 36 is axially captive between the stationary collar 30 and the end socket 16, as best seen in FIGS. 2 and 6.

The motor drive 26 includes a motor housing 38 attached to mounting block 42 which extends radially from collar 30.

Figure 3:
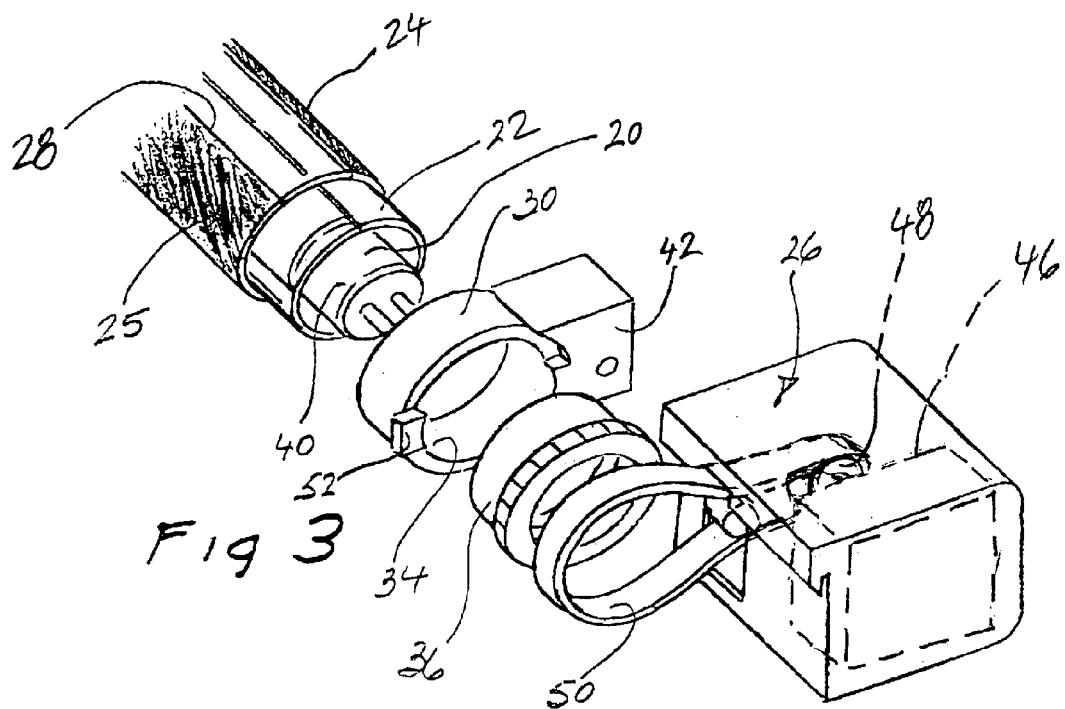
FIG. 3 is an exploded perspective view of the motor drive coupling of FIG. 2.

The motor housing 38 is also supported on mounting plate 44 which is integral with the lamp base 12. An electric motor 46 is mounted in motor housing 38 and turns a motor shaft with a drive pulley 48, as seen in FIG. 3. A drive belt 50 driven by the drive pulley on the motor wraps around and turns the drive ring 36, thereby also turning the color filter tube 22 in collars 30 relative to the aperture mask 24. A radial tab 52 projects from collar 30 into slot 49 of the lamp base 12 to better hold the collar 30 against rotation.

Figure 8:
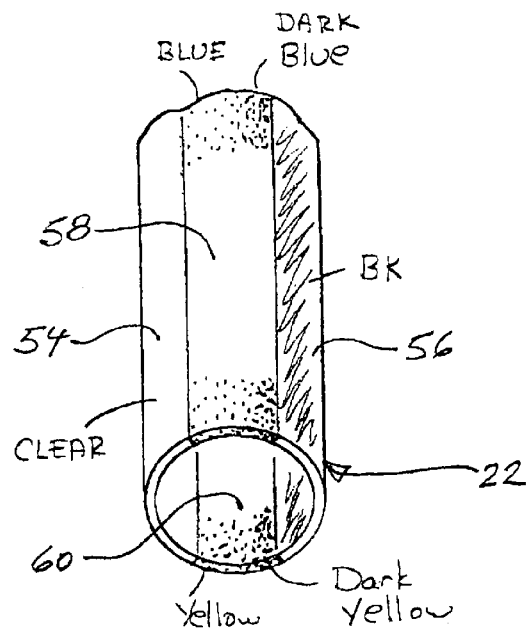
FIG. 8 is a fragmentary side-end perspective view of the four-filter color tube of the light fixture of FIGS. 2 through 6.

As best seen in FIG. 8, the color filter tube 22 has four circumferentially adjacent filter strips extending longitudinally the length of color filter tube 22 and each extending circumferentially about 90 degrees or one-quarter of the circumference of color filter tube 22. The four color filter strips include a generally clear strip 54, a generally opaque strip 56, a first colored strip 58 and a second colored strip 60. The clear and opaque strips are diametrically opposed to each other on color filter tube 22, and the two colored strips 58,60 are also diametrically opposed to each other. The colored strips 58,60 are each interposed in a circumferential direction between the clear and the opaque strips, 54, 56 on diametrically opposite sides of color filter tube 22. The width or circumferential extent of slot aperture 28 on lamp tube 20 is approximately 90 degrees of the tube circumference or somewhat less than 90 degrees.

In an initial operational condition of the lamp fixture 10 the color filter tube 22 is rotationally positioned with the clear strip 54 in registry or alignment with slot aperture 28 (the clear position), so that the light emitted by lamp tube 20 is passed without significant change in color, to provide normal, white light which is associated with a daytime or waking condition of those in the aircraft cabin. At a time when the cabin interior is to darkened in order to allow the occupants to fall asleep, the motor 46 is activated, turning the color filter tube 22 at a slow, generally imperceptible rate of rotation, to bring the opaque strip 56 into alignment with slot aperture 28 (the dark position). In the dark position light from the lamp tube 20 is generally blocked, and little if any light is emitted by the lamp fixture 10. Between the light and the dark positions of the color tube, the first colored filter strip passes into and out of alignment with slot aperture 28. As the clear strip begins to move out of alignment with slot aperture 28 and the first colored strip 58 gradually moves into alignment, the light transmitted by slot aperture 28 is increasingly transmitted through the colored strip 58 so that a blend of white and colored light is emitted from lamp fixture 10. As the color tube continues to turn the clear strip moves entirely out of alignment with slot aperture 28 and all light emitted through the aperture is colored by filter strip 58. As tube rotation continues, the first colored strip 58 also begins to move out of alignment with slot aperture 28 as the opaque strip 56 moves into alignment with the aperture. During this process, slot aperture 28 is increasingly blocked by opaque strip 56 while a diminishing amount of colored light is emitted by the lamp fixture 10 until the dark position is reached and light emission is blocked altogether.

The color of the first colored strip or filter is chosen so as to simulate the tint of the sky after sunset as dark night falls. A presently preferred first color for this purpose is blue to simulate evening twilight. It is also preferred to make the first colored filter of increasing density so that initially a light blue color is presented to slot aperture 28 growing to a deeper blue, eventually fading into darkness as the opaque strip blocks light from the lamp tube 20.

The light fixture 10 is typically left in the dark position during a sleep period of the occupants of the passenger cabin, which may last a number of hours. At the end of the sleep period, when the cabin occupants are to be wakened, The motor 46 is again activated for turning the color tube from the dark position to the clear position at a slow, imperceptible or barely perceptible rate. The opaque strip 56 slowly moves out of registry with slot aperture 28 admitting the second colored strip 60 into alignment with the aperture, so that a gradually increasing amount of light is passed and colored by the second colored strip 60. As the color tube continues rotation towards the clear position, the opaque strip moves entirely out of alignment and is replaced by full alignment of the second colored strip with slot aperture 28, so that an greater amount of light is emitted and all of it is colored by second colored strip 60. This stage is succeeded by a condition where the second colored strip 60 is itself gradually replaced by the clear strip 54, so that the coloring fades as a diminishing amount of light passes through second colored filter strip 60 and more light passes through clear filter strip 54, until the clear position is reached and all light emitted through slot aperture 28 is clear and substantially uncolored.

The color of the second colored strip or filter is chosen so as to simulate the coloring of the sky during sunrise as the sky transitions from darkness to daylight. A presently preferred color for this purpose is yellow, which is suggestive of sunlight. It is preferred to also make the second colored filter of increasing density from the clear to the opaque strips, so that initially a deep yellow color is presented to slot aperture 28 growing to a lighter yellow, the yellow coloring eventually fading into white as the clear strip passes the light from the lamp tube 20.

As an alternative or an adjunct to gradation of the color density of the color filter strips, electronic dimming of the fluorescent lamp tube may be employed to deepen the apparent color of the light in coordination with rotation of the color filter tube 22 to and from the dark position. That is, an increasingly deeper blue light coloring may be achieved by slowly dimming the intensity of the lamp tube 20 as the blue filter strip passes across the mask aperture towards the dark state of the lamp fixture. Conversely, an initially deep yellow coloring may be obtained by dimming the light output of lamp tube 20 as the opaque strip moves out of registry with slot aperture 28 and the yellow filter strip moves into registry. The light output of lamp tube 20 is then gradually increased in step with rotation of the color tube until full light output of the tube is achieved, for example, as the yellow filter has reached full registry with the mask aperture or the clear strip starts to move into partial registry with the light aperture. The use of electronic dimming as just described may render unnecessary the use of color gradient filter strips so that color filter strips of single density are effective for rendering the desired light coloring effects, particularly where a relatively wide mask aperture is employed which is less effective in its selectivity of a particular region of a color gradient on the filter strip.

Coordination of electronic dimming of lamp tube 20 with mechanical rotation of color filter tube 22 is conveniently achieved under program control of a microprocessor or microcontroller connected to the dim level input of a dimmable fluorescent lamp ballast on the one hand, and for driving the motor 46 of the lamp fixture 10 on the other hand. One such microprocessor or microcontroller can be connected for operating multiple lamp fixtures 10 in this manner, thereby to control the accent lighting of an aircraft cabin or a room furnished with a number of such lamp fixtures.

Figure 11:
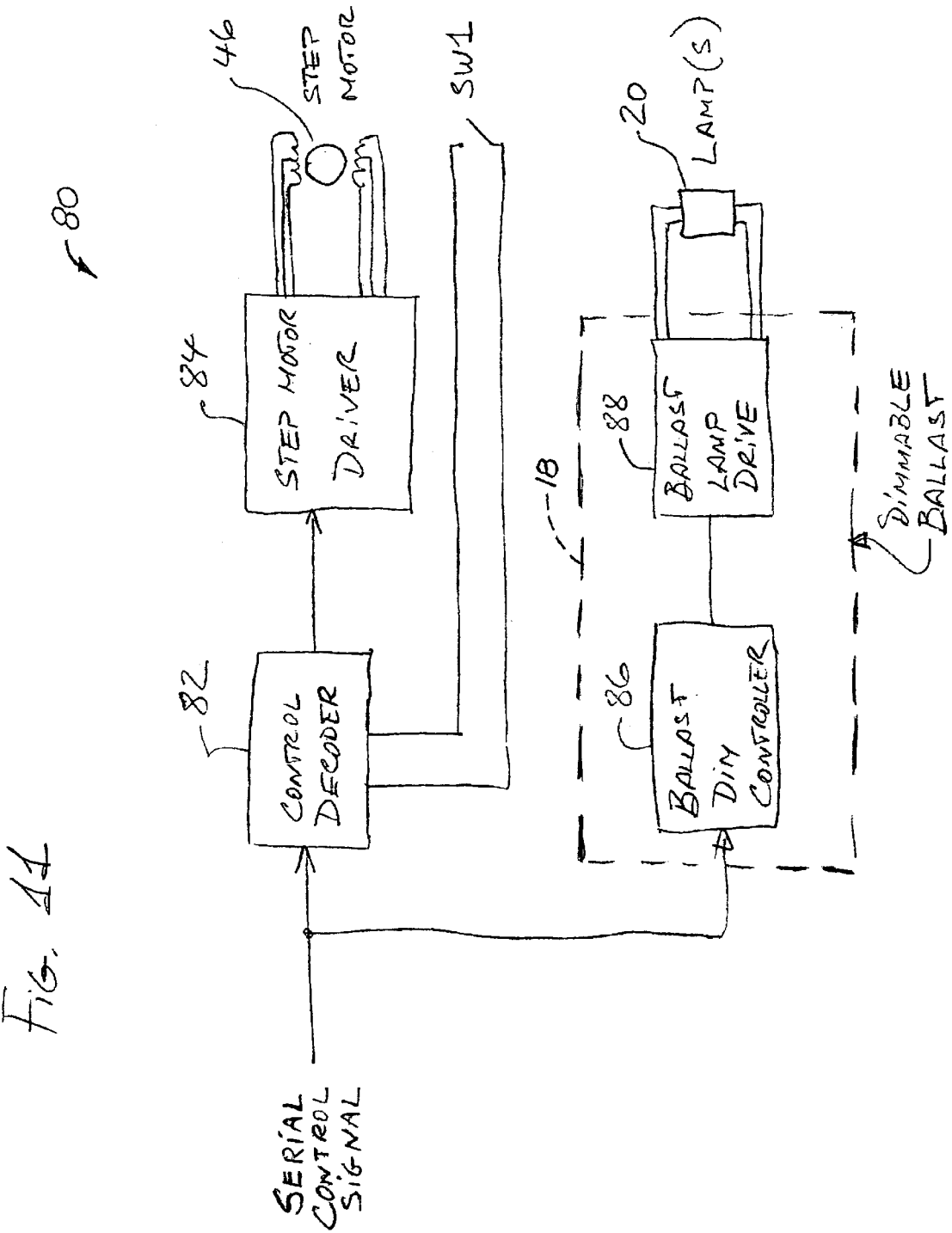
FIG. 11 is a block diagram of a typical electronic control system 80 for the accent light fixture 10.

FIG. 11 is a block diagram of a typical electronic control system 80 for the accent light fixture 10. A serial control signal generated by a suitable controller is input to a control decoder 82. Decoder 82 receives position input of the color filter tube 22 from limit switch SW1 mounted at a convenient location on the lamp fixture for producing a switch signal to the decoder representative of a predetermined rotational position of the color tube. The control decoder delivers a control output to step motor driver 84 which actuates step motor 46 to turn the color tube at a rate and to an extent determined by the serial control signal. The serial control signal is also an input to a ballast dim controller 86 which in turn controls a ballast lamp drive 88 so as to drive the lamp tube 20 to a desired level of light output.

Figure 9:
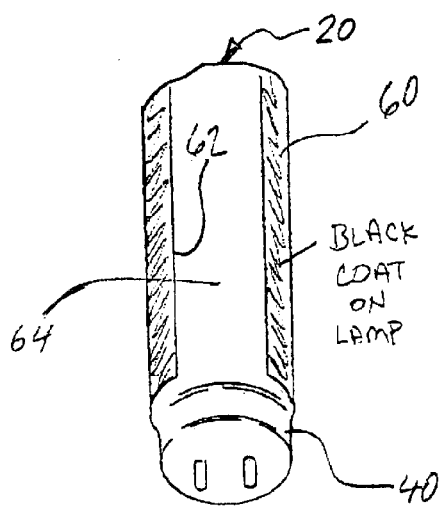
FIG. 9 is a fragmentary perspective view of a linear fluorescent lamp tube equipped with an aperture mask as an alternative to the aperture tube of FIGS. 6 and 7.

FIG. 9 shows an alternative aperture defining mask in the form of an opaque layer 61 applied to the outer surface of the lamp tube 20 so as to define a slot aperture 62 through which is exposed an unblocked strip area 64 of the lamp tube. The opaque layer may be an adhesive sheet material or a light blocking paint, for example, applied to the lamp tube. The alternative mask may also be a tubular material, such as a longitudinally slotted tube, that can be fitted onto the lamp tube, or a cylindrical tube of clear material fitted over the lamp tube and partially covered with light blocking material while leaving a longitudinal clear slot area. It will be appreciated from the foregoing that the aperture defining mask can be interposed between the lamp tube and the color tube so as to limit illumination of the color tube to only a particular circumferential portion of the color tube, so that the light fixture 10 only emits light passed by the selected illuminated circumferential portion of the color tube, or the mask can be exterior to the color tube so as to contain light passed by circumferential portions of the color tube and pass only light filtered by a circumferential portion of the color tube selected by its alignment with the aperture.

Figure 4:
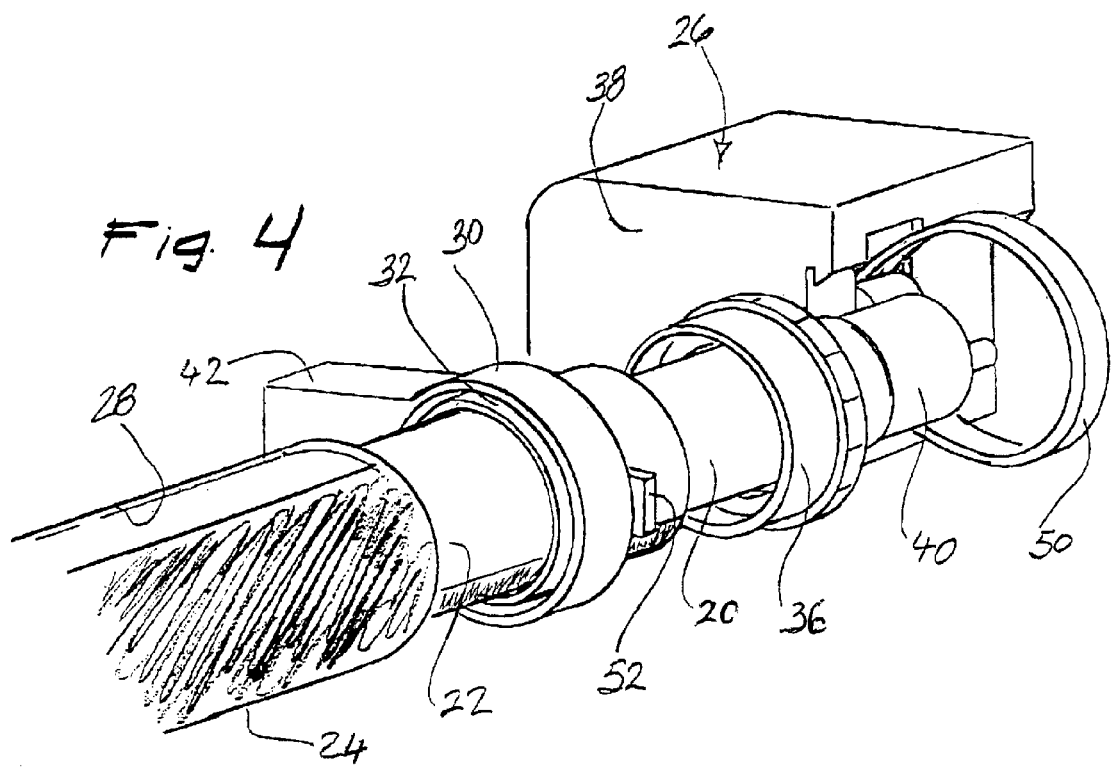
FIG. 4 is an exploded perspective view of the motor drive and color tube bearing collar seen along the length of the color tube.
Figure 5:
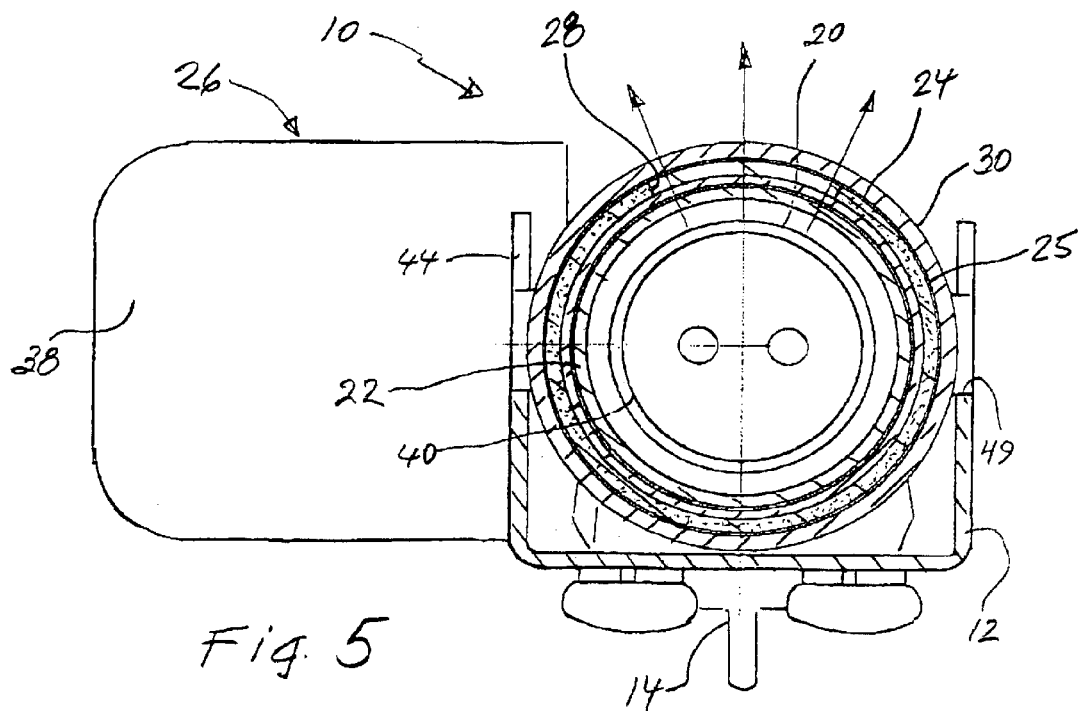
FIG. 5 is a cross sectional view taken along line 5—5 in FIG. 1.
Figure 10:
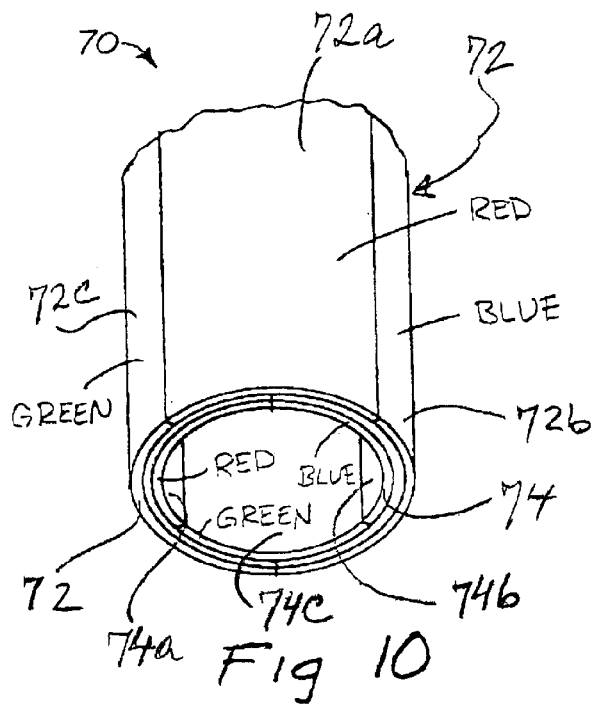
FIG. 10 is an alternative color tube arrangement which includes a part of concentric filter tubes each with a number of color filters which can be brought into arbitrary superposition in alignment with the aperture of the light fixture to obtain a wide range of light output colors.

FIG. 10 depicts an alternate, compound color tube 70 for use in the variable color filter for a linear fluorescent lamp according to this invention. The color tube 70 consists of two concentric primary color tubes 72, 74 each of which has three longitudinally extending and circumferentially adjacent red, blue, green color filter strips 72a, 72b, 72c and 74a, 74b, 74c respectively. Each primary color tube 72, 74 is turned independently of the other color tube by a drive motor relative to a mask aperture dimensioned and positioned in the manner described with regard to the embodiment of FIGS. 2–6. Two drive motors can be provided in a lamp fixture such as shown in FIG. 1, one drive motor at each end of the lamp tube, each motor installed as shown in FIGS. 3 and 4 but one motor turning the outer primary color tube 72 and the other motor turning the inner primary color tube 74 by means of corresponding drive rings which may be similar to drive ring 36. For any arbitrary position of the primary color tubes 72, 74, one color filter or a combination of two adjacent filters on each tube 72, 74 is in alignment with a mask aperture of the color control system of the lamp fixture. These aligned color filters also overlap each other with cumulative filtering action such that the color of light from the lamp tube ultimately passed by both filters is a combination of the overlapping filter colors. By appropriate selection of the aligned color filters on the concentric tubes a large range of light color outputs can be obtained. The range of colors can be further increased by making each of the color filter strips 72a,b,c and 74a,b,c of graduated density so that the relative intensities of the filter colors being combined may be selected by suitable rotational positioning of tubes 72, 74 relative to the mask aperture of the fixture.

In an alternate form of the invention, mechanical dimming of the linear fluorescent light tube 20 is achieved by dispensing with the color filter strips 58, 60 of the color filter tube 22 thereby to provide a dimming tube which is clear about its circumference except for an opaque longitudinal strip of sufficient circumferential dimension to substantially block emission of light when the opaque strip is brought into registry with slot aperture 28, 62. The dimming tube is similar to color filter tube 22 in FIG. 8 except that the color strips 58, 60 are replaced by clear strips, or a single clear area can be provided in place of the three strips 54, 58, 60, leaving only opaque strip 56 on an otherwise clear tube. Initial positioning of the dimming tube, so as to align only the clear portion with the mask aperture, allows substantially unimpeded passage of light emitted by the lamp tube 20 resulting in full intensity illumination by the light fixture 10. Rotation of the dimming tube gradually and increasingly brings the opaque strip into partial registry with the mask aperture, thereby blocking light emission to an increasing extent. When the opaque strip is brought into full registry with the mask aperture, light emission is substantially fully blocked and the lamp fixture is in a dark state even though the lamp tube 20 is turned on. Between the full illumination and dark states of the lamp fixture, precise control of light intensity is readily achieved by rotational positioning of the dimming tube relative to the mask aperture 28, 62. The overlapping mask aperture and movable opaque strip in effect define a continuously variable light aperture which is adjustable to pass a desired degree of illumination from lamp tube 20.

Such mechanical dimming provides an alternative to electronic dimming of fluorescent light tubes which in some cases is difficult to achieve. Some fluorescent lamps have a tendency to flicker when electronically dimmed. It is also difficult to achieve low level dimming of fluorescent lamps because of noticeable flicker or a tendency to extinguish at low levels. Furthermore, the mechanical dimming approach just described allows precise, continuous control over light intensity from fill intensity through very low levels of illumination to full darkness simply by rotational adjustment of the dimming tube so as to increase or decrease the effective aperture defined by the combination of the mask aperture and the opaque strip of the dimming tube. It should be appreciated that the geometry of the opaque and clear areas of the dimming tube need not be in the form of rectilinear strips but may take any form such as to define a variable light aperture by rotation of the dimming tube relative to the mask aperture.

A preferred and alternate embodiments of the invention have been described and illustrated for purposes of clarity and example. However, many changes, modifications and substitutions to the described embodiments will be apparent to those having only ordinary skill in the art without departing from the scope of the invention as defined by the following claims.

What is claimed is:

1. A variable color filter for linear fluorescent lamps comprising:

a color tube supporting a plurality of colored filter strips each disposed longitudinally along said color tube and in circumferentially adjacent relationship to each other, said color tube supported for rotation about a lamp tube;

a motor for rotating said color tube;

a mask defining an aperture for limiting emission of light filtered by only a circumferential portion of said color tube; and control means operatively connected to said motor for selectively positioning said color tube in relation to said aperture thereby to achieve a desired coloring of light emitted by the lamp tube.

2. The variable filter of claim 1 wherein said mask is interposed between said color tube and the said lamp tube.

3. The variable filter of claim 1 wherein said mask is positioned exteriorly to said color tube.

4. The variable color filter of claim 1 wherein said filter strips are of even width with each other.

5. The variable color filter of claim 1 wherein said filter strips are each of a single color.

6. The variable color filter of claim 1 wherein one or more of said filter strips are of varying color density across a strip width.

7. The variable color filter of claim 1 wherein at least one of said strips is substantially opaque to transmission of light.

8. The variable color filter of claim 1 wherein at least one of said strips is substantially clear.

9. The variable color filter of claim 1 wherein said filter strips comprise a substantially opaque strip, a substantially clear strip and one or more colored strips.

10. The variable color filter of claim 9 wherein said one or more colored strips comprise a yellow filter strip and a blue filter strip.

11. The variable color filter of claim 10 wherein said yellow filter strips are of graduated density.

12. The variable color filter of claim 11 wherein said yellow filter strip and said blue filter strip are each of increasing density towards said substantially opaque strip.

13. The variable color filter of claim 1 wherein said filter strips are affixed to said color tube with an adhesive.

14. The variable color filter of claim 1 wherein said filter strips are secured to said color tube by a shrunk wrapper.

15. The variable color filter of claim 1 wherein said filter strips are gel filter strips.

16. The variable color filter of claim 1 wherein said filter strips are dichroic filter strips.

17. The variable filter of claim 1 wherein said filter strips are printed onto a surface of said color tube.

18. The variable filter of claim 1 further comprising an ultra violet filter interposed between said filter strips and the said lamp tube in said color tube.

19. A variable color filter for linear fluorescent lamps comprising:
    a color tube supported for rotation about a lamp tube;
    a motor for rotating said color tube;
    a plurality of colored filter strips each disposed longitudinally along said color tube and in circumferentially adjacent relationship to each other, said filter strips including a substantially opaque strip, a substantially clear strip, a yellow strip and a blue strip;
    a mask defining an aperture for limiting light emission to light filtered by only a circumferential portion of said color tube and colored by one or more of said strips on said circumferential portion; and
    control means operatively connected to said motor for selectively positioning said color tube in relation to said aperture, thereby to achieve a desired coloring of light emitted through said aperture by said lamp.

20. The variable color filter of claim 19 wherein said control means are operative for rotating said color tube from said clear to said opaque and then to said clear at a relatively slow rate not readily perceptible to a human observer thereby to achieve slow changes in illumination suggestive of nightfall and daybreak between color tube positions corresponding to uncolored illumination and darkness.

21. A method for simulating daybreak and nightfall ambient illumination comprising the steps of providing a linear fluorescent lamp including a lamp tube, providing a lamp aperture for emitting light from said lamp tube into an illuminated environment, and filtering light emitted through said aperture through changing filter media of color suggestive of nightfall and daybreak respectively between blocked and unfiltered conditions of the emitted light.

22. The method of claim 21 further comprising an electronic dimming control connected for controlling light output of said lamp tube in coordination with said changing filter media.

23. The method of claim 22 wherein said step of filtering light comprises selectively rotating a plurality of light filters including a substantially clear filter, a substantially opaque filter, a yellow filter and a blue filter.

24. The method of claim 23 wherein said yellow filter and said blue filter are each interposed between said clear filter and said opaque filter.

25. The method of claim 24 wherein said yellow filter and said blue filter are each of increasing density from said clear filter towards said substantially opaque filter.

26. A mechanically dimmable linear fluorescent lamp comprising:
    a light fixture including a fluorescent lamp tube;
    a dimming tube supported for rotation about said lamp tube, said dimming tube having a clear circumferential area and an opaque circumferential area; and
    a mask defining an aperture for limiting emission of light filtered by only a circumferential portion of said dimming tube.

27. The continuously dimmable linear fluorescent lamp of claim 26 further comprising a motor for rotating said dimming tube relative to said mask.

28. The continuously dimmable linear fluorescent lamp of claim 27 further comprising control means operatively connected to said motor for selectively positioning said dimming tube in relation to said aperture thereby to achieve a desired level of illumination by the lamp.

* * * * *